United States Patent [19]

Thevignot

[11] Patent Number: 5,110,946
[45] Date of Patent: May 5, 1992

[54] PREPARATION OF 4-CHLORO-3-SULPHAMOYL-N-(2,3-DIHYDRO-2-METHYL-1H-INDOL-1-YL)-BENZAMIDE FROM 2,3-DIHYDRO-2-METHYL-1H-INDOLE AND HYDROXYLAMINE-O-SULPHONIC ACID

[75] Inventor: Roger Thevignot, Bolbec, France

[73] Assignee: Adir et Compagnie, Courbevoie, France

[21] Appl. No.: 704,309

[22] Filed: May 22, 1991

[30] Foreign Application Priority Data

Jun. 14, 1990 [FR] France .................. 90 07387

[51] Int. Cl.⁵ ........................... C07D 209/08
[52] U.S. Cl. ........................ 548/483; 548/469
[58] Field of Search ...................... 548/483

[56] References Cited

U.S. PATENT DOCUMENTS 3,565,911  2/1971  Beregi ..................... 548/483
4,570,001  2/1986  Auerbach ................. 548/483

FOREIGN PATENT DOCUMENTS 0068239  1/1983  European Pat. Off. ...... 548/483
0124766  7/1983  Japan ..................... 548/483
0124767  7/1983  Japan ..................... 548/483
1203691  9/1970  United Kingdom ......... 548/483

Primary Examiner—Mary C. Lee
Assistant Examiner—Jacqueline Haley
Attorney, Agent, or Firm—Gordon W. Hueschen

[57] ABSTRACT

The invention relates to a new process for the industrial preparation of 4-chloro-3-sulphamoyl-N-(2,3-dihydro-2-methyl-1H-indol-1-yl)benzamide from 2,3-dihydro-2-methyl-1H-indole and hydroxylamine-O-sulphonic acid.

5 Claims, No Drawings

PREPARATION OF 4-CHLORO-3-SULPHAMOYL-N-(2,3-DIHYDRO-2-METHYL-1H-INDOL-1-YL)-BENZAMIDE FROM 2,3-DIHYDRO-2-METHYL-1H-INDOLE AND HYDROXYLAMINE-O-SULPHONIC ACID

The present invention relates to a new process for the industrial preparation of 4-chloro-3-sulphamoyl-N-(2,3-dihydro-2-methyl-1H-indol-1-yl)benzamide.

This compound, which is also known under the INN indapamide, possesses very valuable pharmacological properties. It has, in particular, antihypertensive properties and is used in the treatment of essential arterial hypertension.

Several methods are already known for the preparation of this compound. The processes already described in the literature, however, do not always enable indapamide to be obtained with a satisfactory degree of purity or in a good yield. Furthermore, certain stages of those processes pose problems from the industrial standpoint.

The process for the preparation of 4-chloro-3-sulphamoyl-N-(2,3-dihydro-2-methyl-1H-indol-1-yl)benzamide described in French Patent 2,003,311 consists in obtaining that compound by reacting 4-chloro-3sulphamoylbenzoyl chloride with 1-amino-2,3-dihydro-2-methylindole. The latter compound is prepared in accordance with the process of J. B. Wright and R. E. Willette (J. Med. and Pharm. Chem. 5 811 (1962) which comprises the reduction of the N-nitroso analogue. The yield of the various stages of that process is hardly satisfactory. In addition, that synthesis process results in the production of secondary products, especially nitrosamine compounds, which are compounds having potential toxicity.

Japanese Patent 54-030159 describes a process for the preparation of indapamide from 4-chloro-3-sulphamoyl-N-(2-methylindol-1-yl)benzamide which is converted into indapamide after reduction. That process also leads to the formation of a large number of secondary products, and several purifications are necessary to obtain a pharmaceutical quality product.

Another process for the preparation of indapamide is described in European Patent 54 892. That process consists in cyclising 1-allyl-1-phenyl-2-(3-sulphamoyl-4chlorobenzoyl)hydrazine in the presence of Lewis or Bronsted acids. That cyclisation also results in the formation of a large number of secondary products, and the yield of the process is hardly satisfactory.

In view of the therapeutic value of indapamide, and the lack of an industrial process enabling it to be obtained with a satisfactory degree of purity, a good yield and, if possible, from fairly inexpensive commercially available starting materials, more detailed research has been carried out and has lead to the discovery of a new process for the preparation of 4-chloro-3-sulphamoyl-N-(2,3-dihydro-2-methyl-1H-indol-1yl)benzamide. The final stage of this process is similar to that described in French Patent 2,003,311 but it has two great advantages: it requires fewer stages and the preparation of 1-amino-2,3-dihydro-2-methyl-1H-indole is carried out without the formation of the N-nitroso analogue. The industrial application of this process is accordingly very advantageous.

The present invention relates more especially to a process for the industrial synthesis of 4-chloro-3-sulphamoyl-N-(2,3-dihydro-2-methyl-1H-indol-1-yl)-benzamide, the compound of the formula I:

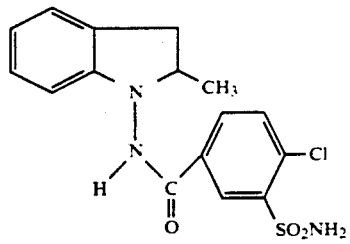

characterised in that 2,3-dihydro-2-methyl-1H-indole, the compound of the formula II:

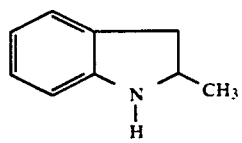

is subjected to the action of hydroxylamine-O-sulphonic acid, the compound of the formula III:

in the presence of triethylamine and at a temperature of from 20° C. to 60° C., then 1-amino-2,3-dihydro-2-methyl-1H-indole, the compound of the formula IV:

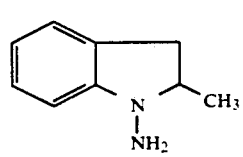

is separated from the reaction medium by selective extraction and is reacted in the form of a base or salt, in solution in tetrahydrofuran or in an alcoholic medium and in the presence of an acid-acceptor with 4-chloro-3sulphamoylbenzoyl chloride, the compound of the formula V:

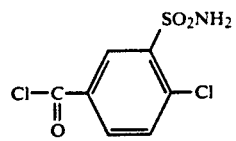

at a temperature of from 20° to 30° C. in order to form the compound of the formula I.

In the preparation of 1-amino-2,3-dihydro-2-methyl-1H-indole, the ratio of the molar amount of hydroxylamine-O-sulphonic acid to the molar amount of 2,3-dihydro-2-methyl-1H-indole reacted must be from 1:1 to 5:1, and preferably from 1.5:1 to 2.5:1.

The reaction is carried out in the presence of an equimolar amount of triethylamine in relation to hydroxylamine-O-sulphonic acid (1.5 mol per 1 mol of 2,3-dihydro-2-methyl-1H-indole). Methylene chloride, dichloroethane, chloroform or other low molecular weight polyhalogenated alkanes ($C_1$-$C_5$) may be used as solvent. The duration of the reaction depends on the temperature at which the reaction is carried out.

At 24° C., to obtain a satisfactory yield, the duration of the reaction has to be approximately 24 hours while at 50° C. 4 hours are necessary.

Hydroxylamine-O-sulphonic acid is a commercial product (Aldrich ®, Janssen ®).

At the end of the reaction, after alkalinisation of the reaction medium using a strong mineral base, 1-amino-2,3-dihydro-2-methyl-1H-indole is isolated from the organic phase (decantation and back-extraction).

The 1-amino-2,3-dihydro-2-methyl-1H-indole so obtained can be converted into a salt before being used for the preparation of indapamide. Hydrochloric acid or methanesulphonic acid is preferably used for the conversion into a salt.

The reaction of 1-amino-2,3-dihydro-2-methyl-1H-indole with 4-chloro-3-sulphamoylbenzoyl chloride is carried out in the presence of an excess of triethylamine. Tetrahydrofuran or another chemically equivalent solvent may be used as reaction solvent.

A detailed, non-limiting description of the implementation of the process of the invention is given hereinafter.

EXAMPLE 1

Preparation of 1-amino-2,3-dihydro-2-methyl-1H-indole and its hydrochloride 22.27 g of hydroxylamine-O-sulphonic acid suspended in 22 ml of methylene chloride are introduced under a stream of nitrogen into a reactor purged with nitrogen.

17.5 g of 2,3-dihydro-2-methyl-1H-indole and 19.98 g of triethylamine in solution in 10 ml of methylene chloride are then poured in over a period of 1 hour at 24° C.

The reaction is allowed to continue for 24 hours and then 100 ml of a mixture of water and concentrated ammonia (80 : 20 v/v) are added with cooling. The whole is stirred for 15 minutes and then decanted, and the organic phase is recovered and the aqueous phase is reextracted with 20 ml of methylene chloride.

The organic phases are combined and washed with 30 ml of water.

The methylene chloride is removed in vacuo using a rotary evaporator to obtain 1-amino-2,3-dihydro-2-methyl-1H-indole.

Yield: 78%

Melting point: 37°–38° C.

The residue is taken up in 140 ml of toluene, under nitrogen and with cooling, and 14 ml of 12N hydrochloric acid are added dropwise. The whole is stirred for 2 hours at from 20° to 22° C., then filtered and washed with toluene.

The filter residue is made into a paste again mechanically for 30 minutes with 50 ml of a mixture of toluene and acetonitrile (15 : 45 v/v). The whole is filtered and dried in an oven.

Purity of the 1-amino-2,3-dihydro-2-methyl-1H-indole hydrochloride: 99.3 % (GLC)

EXAMPLE 2

Preparation of 4-chloro-3-aminosulphonyl-N-(2,3-dihydro2-methyl-1H-indol-1-yl)benzamide 800 ml of tetrahydrofuran and 0.2045 mol of 1-amino-2,3-dihydro-2-methyl-1H-indole hydrochloride are introduced into a reactor purged with nitrogen. 0.4328 mol of triethylamine is then poured in over a period of 10 minutes. The reaction solution is then stirred at from 18° to 20° C. for 30 minutes. 0.2050 mol of 4-chloro-3sulphamoylbenzoyl chloride in solution in 400 ml of tetrahydrofuran is then added dropwise over a period of 1 hour 45 minutes.

The reaction medium is stirred for 3 hours at from 24° to 30° C. and then 0.5 g of black $CN_1$ ® is added. The whole is filtered and the filtrate is concentrated.

The residue after evaporation is then recrystallised from isopropanol.

Yield: 80.5%

Purity (HPLC): 99.98%

I claim:

1. Process for the preparation of 4-chloro-3-sulphamoyl-N-(2,3-dihydro-2-methyl-1H-indol-1-yl)benzamide, the compound of the formula I:

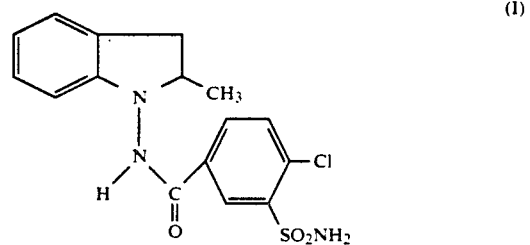

characterised in that 2,3-dihydro-2-methyl-1H-indole, the compound of the formula II:

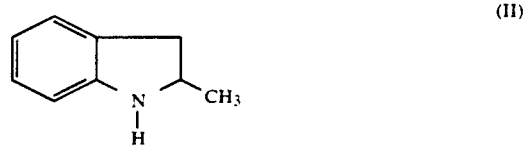

is subjected to the action of hydroxylamine-O-sulphonic acid, the compound of the formula III:

$$H_2NOSO_3H \qquad (III)$$

is suspended in a polyhalogenated alkane, in the presence of triethylamine and at a temperature of from 20° C. to 60° C., then 1-amino-2,3-dihydro-2-methyl-1H-indole, the compound of the formula IV:

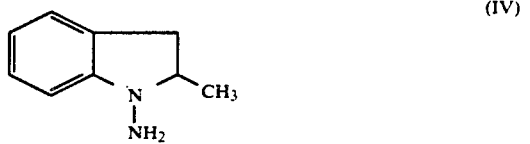

is separated from the reaction medium by selective extraction and is reacted in the form of a base or salt, in solution in tetrahydrofuran or in an alcoholic medium and in the presence of an acid-acceptor with 4-chloro-3-sulphamoylbenzoyl chloride, the compound of the formula V:

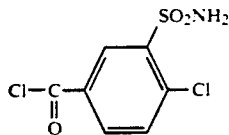

at a temperature of from 20° to 30° C. in order to form the compound of the formula I.

2. Process according to claim 1, characterised in that the 2,3-dihydro-2-methyl-1H-indole is in solution in methylene chloride or in dichloroethane.

3. Process according to claim 1, characterised in that the ratio of the molar amount of hydroxylamine-O-sulphonic acid to the molar amount of 2,3-dihydro-2-methyl-1H-indole reacted is from 1:1 to 5:1.

4. Process according to claim 1, characterised in that the reaction of hydroxylamine-O-sulphonic acid with 2,3-dihydro-2-methyl-1H-indole is carried out at a temperature of from 20° to 60° C.

5. Process according to claim 1, characterised in that the 1-amino-2,3-dihydro-2-methyl-1H-indole is reacted in the form of a hydrochloride or a methanesulphonate with the 4-chloro-3-sulphamoylbenzoyl chloride.

* * * * *

UNITED STATES PATENT AND TRADEMARK OFFICE
CERTIFICATE OF CORRECTION

PATENT NO. : 5,110,946

DATED : May 5, 1992

INVENTOR(S) : Roger Thevignot

It is certified that error appears in the above-identified patent and that said Letters Patent is hereby corrected as shown below:

Column 1, line 25; "3sul-" should read -- 3-sul- --.

Column 1, line 46; "4chlorobenzoyl" should read
    -- 4-chlorobenzoyl --.

Column 1, line 57; "1yl" should read -- 1-yl --.

Column 2, line 44; "3sulphamoylbenzoyl" should read
    -- 3-sulphamoylbenzoyl --.

Column 3, approximately line 62; "dihydro2" should read
    -- dihydro-2 --.

Column 4, line 2; "3sulphamoylbenzoyl" should read
    -- 3-sulphamoylbenzoyl --.

Signed and Sealed this

Third Day of November, 1992

Attest:

DOUGLAS B. COMER

Attesting Officer

Acting Commissioner of Patents and Trademarks